United States Patent
Ohtawa et al.

(10) Patent No.: US 6,855,682 B2
(45) Date of Patent: Feb. 15, 2005

(54) SOFTENER COMPOSITION

(75) Inventors: Yasuki Ohtawa, Wakayama (JP); Takeshi Tomifuji, Wakayama (JP); Akira Sakaguchi, Wakayama (JP); Tohru Katoh, Wakayama (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 10/092,983

(22) Filed: Mar. 8, 2002

(65) Prior Publication Data

US 2003/0036499 A1 Feb. 20, 2003

(30) Foreign Application Priority Data

| Mar. 8, 2001 | (JP) | 2001-065090 |
| Mar. 8, 2001 | (JP) | 2001-065091 |
| Mar. 28, 2001 | (JP) | 2001-093069 |

(51) Int. Cl.$^7$ .............................................. C11D 1/835
(52) U.S. Cl. ...................................................... 510/515
(58) Field of Search ................................ 510/499, 507, 510/515, 504

(56) References Cited

U.S. PATENT DOCUMENTS

| 4,137,180 A | 1/1979 | Naik et al. |
| 4,948,520 A | 8/1990 | Sasaki |
| 5,296,622 A * | 3/1994 | Uphues et al. ............. 554/103 |
| 5,854,201 A | 12/1998 | Behler et al. |

FOREIGN PATENT DOCUMENTS

| DE | 1935499 | 1/1971 |
| DE | 19904233 A1 | 8/2000 |
| EP | 0002857 A1 | 7/1979 |
| EP | 675 941 | 10/1995 |
| EP | 0707059 A2 | 4/1996 |
| GB | 1585383 | 3/1981 |
| JP | 09255988 | 9/1997 |
| WO | WO91/01295 A1 | 2/1991 |
| WO | WO 97/42279 | 11/1997 |
| WO | WO97/45514 A1 | 12/1997 |
| WO | WO99/27046 | 6/1999 |
| WO | WO99/27050 | 6/1999 |
| WO | WO 01/32813 | 5/2001 |

* cited by examiner

*Primary Examiner*—John R. Hardee
(74) *Attorney, Agent, or Firm*—Birch, Stewart, Kolasch & Birch, LLP

(57) ABSTRACT

A softener composition, which contains tri-long-chain alkyl quaternary ammonium salt that has been considered to be difficult to use as a softener base agent, and which can provide a softener composition that provides a sufficient softening performance, is provided with (A) a cationic surfactant comprising at least one selected from the group consisting of quaternary ammonium salts represented by the formulae (I), (II) or (III), wherein the ratio of quaternary ammonium salt represented by the formula (I) to the total amount of these salts exceeds 50 weight %, with the ratio thereof represented by (III) being set to not more than 10%, and (B) at least one nonionic surfactant. In this case, (A) may include tertiary amine.

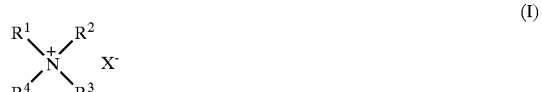

(I)

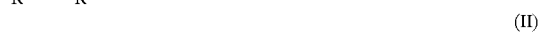

(II)

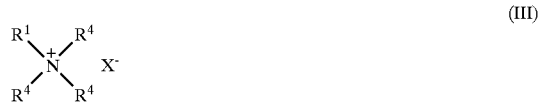

(III)

(wherein, $R^1$, $R^2$ and $R^3$ represent long-chain alkyl groups, etc. having total carbon atoms of 8 to 40, which may be intersected by an ether group, an ester group or an amide group; $R^4$ represents an alkyl group, etc. having carbon atoms of 1 to 6, and $X^-$ represents an anionic group.)

8 Claims, No Drawings

SOFTENER COMPOSITION

FIELD OF THE INVENTION

The present invention relates to a preparation method of quaternary ammonium salt that is desirably used as a softener base agent, quaternary ammonium salt obtained through such a preparation method and a softener composition containing such salt that exhibits superior softness.

BACKGROUND OF THE INVENTION

In recent years, most of the products that are commercially available as the fiber-use softener have a composition containing quaternary ammonium salt having two long-chain alkyl groups in each molecule, as typically represented by di(long-chain alkyl)dimethyl ammonium chloride. However, the quaternary ammonium salt of this type has a problem in which, when its residual substances after use are discharged into the natural field, most of them are accumulated without being subjected to biodegradation.

In order to solve this problem, N-methyl-N,N-bis(long-chain alkanoyl oxyethyl)-N-(2-hydroxyethyl) ammonium methylsulfate or the like has been introduced to the market as modified products. In comparison with the above-mentioned quaternary ammonium salt, this product has better biodegradability.

N-methyl-N,N-bis(long-chain alkanoyl oxyethyl)-N-(2-hydroxyethyl) ammonium methylsulfate is prepared by esterifying triethanol amine using a long-chain fatty acid and successively quaternizing this by dimethyl sulfate. The reaction molar ratio of fatty acid to triethanol amine is normally set to 1.8 to 2.1, and in this case, the ratio of diester quaternary salt to the total amount of monoester quaternary salt, diester quaternary salt and triester quaternary salt is 43 to 47 weight %. The reaction molar ratio is set to 1.8 to 2.1 because at this time, the ratio of diester quaternary salt is maximized, and the reaction molar ratio smaller than 1.8 or greater than 2.1 causes a reduction in the ratio of diester quaternary salt, resulting in degradation in the softening performance. However, even when the reaction molar ratio is set within 1.8 to 2.1, it is not necessarily possible to provide a sufficient softening property.

In order to solve the above-mentioned problem, WO9742279 has disclosed quaternary ammonium salt in which the ratio of diester quaternary salt is not less than 55 weight % with the ratio of triester quaternary salt being set to not more than 25 weight %, and the preparation method thereof. Although this product has an improved softening performance, it has not been a satisfactory product.

Most of the other softener base agents have the di-long-chain alkyl quaternary ammonium salt structure, and with respect to tri-long-chain alkyl quaternary ammonium salt, the application thereof as a softener base agent has not been proposed because of the reasons that more hydrophilic groups exist in comparison with lipophilic groups with insufficient dispersing property to water with the result that the softening performance is not sufficiently exerted.

Moreover, such quaternary ammonium salt is prepared by allowing the corresponding tertiary ammine to react with a quaternizing agent and at the time of the quaternizing reaction, alcohol solvents such as isopropyl alcohol and ethanol are generally used. However, alcohol based solvents have a low flash point which causes a risk of a fire, and also have inherent odor causing adverse effects on odor of the products containing these base agents, and these do not function as effective components for softening cloth and hair, etc., resulting in the corresponding additional costs. However, without the application of such a solvent, the melting point of quaternary ammonium salt becomes higher, resulting in another problem with handling.

The objective of the present invention is to provide a softener composition which contains tri-long-chain alkyl quaternary ammonium salt that has been considered to be difficult to use as a softener base agent, and which provides a sufficient softening performance.

EP-A675941 and WO97/42279 disclose a mixture of quaternary ammonium salts including 50% or more of a triester-having quaternary ammonium salt.

WO01/32813 and JP-A 2001-131871 disclose a mixture of quaternary ammonium salts including 15 to 85% of a tri-ester-having quaternary ammonium salt, up to 40% of a di-ester-having quaternary ammonium salt and 15 to 85 of a mono-ester-having quaternary ammonium salt for a for a softener. DE-A 1935499 discloses production of a tri-ester-having quaternary ammonium for softener, in Example 2.

DISCLOSURE OF THE INVENTION

The objective of the present invention is to provide a softener composition that contains tri-long-chain alkyl quaternary ammonium salt and is excellent in softening property and biodegradability. This composition also has a good property in fish toxicity testing.

Therefore, the purpose of the present invention is also to provide an efficient preparation method of a quaternary ammonium salt that is excellent in softener base agent and have a good biodegradability.

The present invention provides a softener composition comprising the following components (A) and (B): (A): a cationic surfactant comprising at least one selected from the group consisting of quaternary ammonium salts represented by the formulae (I), (II) or (III), wherein the ratio of the quaternary ammonium salt represented by the formula (I) to the total amount of the quaternary ammonium salts represented by the formulae (I), (II) and (III) exceeds 50 weight % and the ratio of (III) to the sum total of (I), (II) and (III) is not more than 10%:

(I)

(II)

(III)

wherein $R^1$, $R^2$ and $R^3$ represent a long-chain alkyl or alkenyl group having the total carbon atoms of 8 to 40, which are the same as or different from one another and may be intersected by an ether group, an ester group or an amide group; $R^4$ represents an alkyl group, an alkenyl group or a hydroxy alkyl group, having 1 to 6 carbon atoms, plural $R^4$'s being the same as or different from one another; and $X^-$ represents an anionic group, (B): a nonionic surfactant that is a compound represented by the following formula (IV):

$R^5COO\text{—}(AO)m\text{—}R^6$ (IV)

wherein, $R^5$ represents an alkyl or alkenyl group having the total carbon atoms of 7 to 29, $R^6$ represents an alkyl or alkenyl group having 1 to 6 carbon atoms, A represents an alkylene group having 2 to 4 carbon atoms and m is a number of 1 to 40 on the average value and plural A's may be the same as or different from one another.

Moreover, the present invention provides a softener composition comprising the following components (A') and (B'):
(A'): a cationic surfactant comprising at least one selected from the group consisting of quaternary ammonium salts represented by the formulae (I), (II) or (III) as defined in claim 1 and at least one selected from the group consisting of amines or salts thereof represented by the following formulae (V), (VI) or (VII), where the ratio of the total mole number of the quaternary ammonium salts to the total molar number of amines or the salts thereof is 99.9:0.1 to 70:30 and the ratio of the quaternary ammonium salts represented by the formula (I) to the total amount of the quaternary ammonium salts represented by the formulae (I), (II) and (III) exceeds 50 weight % and the ratio of (III) to the sum total of (I), (II) and (III) is not more than 10%:

(V)

(VI)

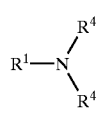

(VII)

wherein $R^1$, $R^2$, $R^3$ and $R^4$ are the same as described above),
(B'): at least one nonionic surfactant selected from the group consisting of compounds represented by the formula (IV) as defined in claim 1 and the following formulae (VIII) or (IX):

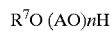

(VIII)

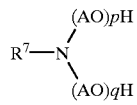

(IX)

wherein, $R^7$ represents an alkyl group, an alkenyl group or an acyl group, having carbon atoms of 8 to 22, A represents an alkylene group having 2 to 4 carbon atoms, n represents a number of 4 to 100 on the average value, p and q are a number of 1 to 50 on the average value, being the same as or different from each other, and plural A's may be the same as or different from one another.

The compounds having the formulae (VIII) and (IX) preferably have an HLB value of 9–17, more preferably 10–16.

The incorporation of the amine compounds (V), (VI) or (VII) or a salt thereof provides the resulting softener composition with a good feeling in touch of chemical fabric in addition to cotton fabric.

The ratio of the total mole number of the quaternary ammonium salts represented by the formulae (I), (II) and (III) to the total mole number of amine salts represented by the formulae (V), (VI) or (VII) is preferably 99:1 to 80:20.

$R^1$, $R^2$ and $R^3$ are the same as or different from one anther and are preferably groups represented by the following formula (X) or (XI):

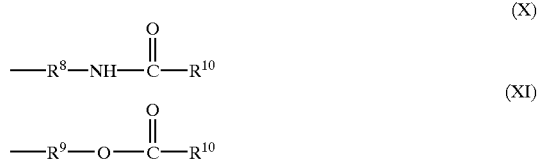

wherein, $R^8$ and $R^9$, which are the same as or different from each other, represent an alkylene group having 2 to 6 carbon atoms and $R^{10}$CO represents a residual group resulting from a fatty acid having 8 to 30 carbon atoms from which a hydroxyl group has been excluded.

The surfactant that is a compound represented by the formula (IV) has preferably an HLB of 9 to 17.

The blending ratio of component (A) to component (B) or component (A') to component (B') is preferably (A)/(B) or (A')/(B') by weight of 50/1 to 1/2.

The blending ratio of component (A) or (A') to the composition is preferably 3 to 50 weight %.

The present invention provides a method of preparing any one of the above-mentioned softener compositions, comprising, first, comprising a composition having the total amount of component (A) and component (B) or component (A') and component (B') of not less than 70 weight % and then mixing it with water.

The present invention provides a method for preparing quaternary ammonium salts represented by the above-mentioned formula (I), (II) or (III), comprising reacting a tertiary amine represented by the above-mentioned formula (V), (VI) or (VII) with a quaternizing agent to prepare a quaternary ammonium salt in at least one aprotic solvent selected from the group consisting of ketone compounds, hydrocarbon compounds, heterocyclic compounds and compounds represented by the following formula (XII):

(XII)

wherein $R^{11}$ and $R^{12}$, which are the same as or different from each other, present alkyl groups, alkenyl groups or acyl groups, each having carbon atoms of 1 to 30, A represents an alkylene group having carbon atoms of 2 to 4, n represents a number of 1 to 40 on the average and n A's may be the same as or different from one another.

The aprotic solvent is preferably a compound represented by the formula (XII). Moreover, the compound represented by the formula (XII) is more preferably a compound represented by the formula (IV):

(IV)

wherein, $R^5$, $R^6$, A and m are defined as the same as described above.

DETAILED DESCRIPTION OF THE INVENTION

[(A) Component]

In order to provide sufficient softness, the component (A) of the composition of the present invention is designed so that the ratio of quaternary ammonium salt represented by the formula (I) to the total amount of quaternary ammonium salts represented by the formulae (I), (II) or (III) (hereinafter, respectively referred to as quaternary ammonium salts (I), (II), (III)) exceeds 50 weight %. More preferably, this value is set to not less than 85 or 90 weight %.

In the quaternary ammonium salts represented by the above-mentioned formula (I), (II) or (III) constituting the component (A) (hereinafter, respectively referred to as quaternary ammonium salts (I), (II), (III)), with respect to $R^1$, $R^2$ and $R^3$, groups represented by the formula (X) or (XI) are preferably used.

In the formulae, $R^8$ and $R^9$, which are the same or different, are alkylene groups having carbon atoms of 2 to 6, more preferably, 2 to 3, and $R^{10}CO$ represents a residual group resulting from a fatty acid having carbon atoms of 8 to 30, more preferably, 12 to 24, from which a hydroxyl group has been excluded.

With respect to $R^4$, an alkyl group or a hydroxyalkyl group having carbon atoms of 1 to 3 is preferably used, and a methyl group, an ethyl group or a hydroxyethyl group is more preferably used. With respect to $X^-$, a halogen ion such as a chloride ion, or an alkylsulfate ion derived from methylsulfate, ethylsulfate, etc. is preferably used.

The method for preparing the cationic surfactant that is the component (A) of the present invention is not particularly limited. For example it can be prepared by quaternizing the product obtained by reacting an alkanol amine, an aminoalkyl amine or the like with an fatty acid or an ester thereof.

With respect to alkanol amine, aminoalkyl amine or the like, preferable examples include: triethanol amine, triisopropanol amine, N,N-bis(2-hydroxyethyl)propanediamine, and N,N-bis(2-hydroxypropyl) propanediamine. With respect to fatty acid and its ester, preferable examples include: tallow fatty acid, hydrogenated tallow fatty acid, palm stearic acid, hydrogenated palm stearic acid or long-chain fatty acids of a mixture of two or more of these having carbon atoms of 8 to 30, more preferably, 12 to 24, or lower alkyl esters thereof, or fats and oils. With respect to the quaternizing agent, dimethylsulfate, diethylsulfate, methylchloride, etc. are preferably used.

As the reaction molar ratio of the fatty acid or its ester to alkanol amine, aminoalkyl amine, etc. is increased, the ratio of quaternary ammonium salt (I) becomes greater; therefore, for example, in the case when triethanol amine and tallow fatty acid are used as materials, the molar ratio of the fatty acid or its ester to triethanol amine is preferably set to not less than 2.7, more preferably, 2.7 to 2.8.

With respect to quaternary ammonium salt (I), examples thereof include: N-methyl-N,N,N-tri(long-chain alkanoyloxyethyl) ammonium salt, N-methyl-N,N-di(long-chain alkanoyloxyethyl)-N-long-chain alkanoylaminopropyl ammonium salt, N-methyl-N,N-di(long-chain alkanoyloxyethyl)-N-long-chain alkanoylaminoethyl ammonium salt, N-methyl-N,N-di(long-chain alkanoyloxyethyl)-N-long-chain alkyl ammonium salt and N-methyl-tri-long-chain alkyl ammonium salt. Those having the long-chain alkanoyloxy group and/or long-chain alkanoylamino group are preferably used because of its superior biodegradability.

With respect to quaternary ammonium salts (I), (II), (III), the quaternary ammonium salts respectively represented by formulae (I-1), (I-2), (II-1), (II-2), (III-1) and (III-2) are more preferably used.

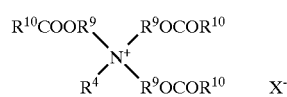

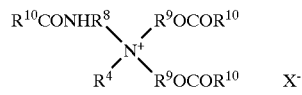

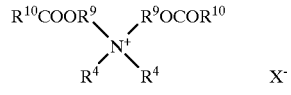

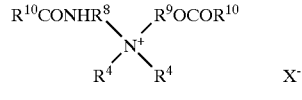

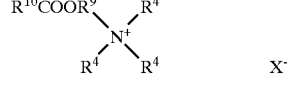

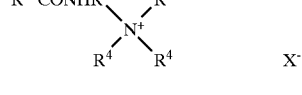

In the formulae, $R^4$, R8, $R^9$, $R^{10}CO$ and $X^-$ are defined as the same as described above.

[(B) Component]

With respect to alkylene oxide adducts of fatty acid ester of component (B), those having an HLB of 9 to 17, more preferably, 10 to 16, are preferably used. Here, HLB is a value obtained from Griffin equation described in "W. C. Griffin, J. Soc. Cosmet. Chemists, 5, 249 (1954)."

With respect to alkylene oxide adducts of fatty acid ester, examples thereof include those obtained by adding alkylene oxide to lower alkyl ester (with alkyl group having carbon atoms of 1 to 3) of long-chain fatty acid having carbon atoms of 8 to 30, more preferably, 12 to 24, such as tallow fatty acid, hydrogenated tallow fatty acid, palm stearic acid, hydrogenated palm stearic acid or mixtures of not less than two kinds selected from these, and those obtained by adding alkylene oxide to lower alcohol such as methanol, ethanol and isopropanol, and then esterifying these by using the above-mentioned long-chain fatty acid or its lower alkyl ester. With respect to the alkylene oxide to be added, ethylene oxide, propylene oxide, etc. are listed, and ethylene oxide is more preferably used. The average added molar number of alkylene oxide is preferably set to 5 to 100, more preferably, 10 to 30.

At least one kind selected from the group consisting of compounds represented by the above-mentioned formula (VIII) or (IX), more preferably, formula (VIII), is preferably used.

In formula (VIII) or (IX), R is preferably prepared as an alkyl group, an alkenyl group or an acyl group having carbon atoms of 12 to 20, more preferably, an alkyl group or an alkenyl group having carbon atoms of 16 to 18. A is preferably prepared as an ethylene group or a propylene group, more preferably, an ethylene group. Here, n is preferably a number of 8 to 20, and p and q, which are the same or different, are preferably set to 4 to 20.

[Softener Composition]

The blending ratio of the (a) component and (b) component of the softener composition of the present invention is preferably set to (a)/(b)(weight ratio)=50/1 to 1/2, more preferably, 20/1 to 1/1. Moreover, the amount of blend of (a) component in the composition is preferably set to 3 to 50 weight %, more preferably, 4 to 30 weight %.

The (a) component and (b) component may be separately incorporated in a softener composition. It is more preferable to mix (a) and (b) with each other in advance to blend them simultaneously. By dispersing these (a) and (b) components to water, it is possible to form a liquid softener.

The softener composition of the present invention is preferably prepared by preliminarily obtaining a composition containing the component (A) and component (B) the total amount of which accounts for not less than 70 weight %, and then mixing this with water. In particular, it is preferable to mix the component (A) and component (B) in a completely dissolved state or molten state with water, and it is more preferable to mix these with water having a temperature not less than the melting point of the mixture of the component (A) and component (B). The amount of water to be mixed is preferably set to such an amount as to finally set the total amount of the component (A) and component (B) in the softener composition to 3.1 to 60 weight %.

To the softener composition of the present invention, a nonionic surfactant other than the component (B) may be added, in order to improve the dispersing property and storage stabilizing property. Moreover, the following components may be added thereto on demand: fatty alcohol (more preferably, including carbon atoms of 8 to 24) or higher fatty acid (more preferably, including carbon atoms of 8 to 24) in order to further improve the softness, lower alcohol such as ethanol or isopropanol, glycol, polyol and ethylene oxides and propylene oxides of these that are added as storage stabilizers, and inorganic salts, pH adjusting agents, hydrotropic agents, perfumes, antifoamers, pigments, etc.

The description of the above-mentioned compositions is also applied to compositions containing the components (A') and (B').

In the present invention, the quaternizing reaction is preferably carried out by adding an aprotic solvent using a tertiary amine and executing a quaternizing process using a quaternizing agent.

[Aprotic solvent]

The aprotic solvent used in the present invention is selected from the group of compounds consisting of ketone compounds, hydrocarbon compounds, heterocyclic compounds and compounds represented by the formula (XII), and these may be liquid or solid matters at room temperature (25° C.) as long as they are liquids at the time of the quaternizing process. More specifically, examples thereof include ketone compounds such as acetone and methylethyl ketone, hydrocarbon compounds such as pentane, hexane, heptane, octane, nonane and decane, heterocyclic compounds such as tetrahydrofuran and dioxane, and compounds represented by the formula (XII); and compounds represented by the formula (XII) are preferably used since they have superior miscibility with water and also have preferable odor in the resulting quaternary ammonium salt.

In the formula (XII), the acyl group is preferably an acyl group derived from a long-chain fatty acid having carbon atoms of 8 to 30, more preferably, 12 to 24, such as tallow fatty acid, hydrogenated tallow fattyacid, palm stearic acid, hydrogenated palm stearic acid or a mixture of two or more kinds selected from these. A is preferably prepared as an ethylene group or a propylene group, more preferably, an ethylene group. Here, n is preferably set to 1 to 30, more preferably, 5 to 30.

With respect to the compound represented by the formula (XII), compounds represented by the following formulae (IV), (VIII) to (XVI) are listed, and compounds represented by the formula (IV) or (XIII) are more preferably used, and most preferably, compounds represented by the formula (IV) are used, because of superior affinity to water, preferable odor generatiod by the resulting quaternary ammonium salt and compatibility for use as a dispersant of the softener.

$R^5COO—(AO)m—R^6$ (IV)

$R^5COO—(AO)m—COR^{13}$ (XIII)

$R^{14}O—(AO)m—R^{15}$ (XIV)

$R^{16}COO—(AO)m—R^6$ (XV)

$R^{16}COO—(AO)m—COR^{17}$ (XVI)

(wherein, $R^5$ and $R^{13}$, which are the same or different, represent alkyl groups or alkenyl groups having carbon atoms of 7 to 29, preferably, 11 to 23, $R^6$, $R^{14}$ and $R^{15}$, which are the same or different, represent alkyl groups or alkenyl groups having carbon atoms of 1 to 6, preferably, 1 to 5, $R^{16}$ and $R^{17}$, which are the same or different, represent alkyl groups or alkenyl groups having carbon atoms of 1 to 5, preferably, 1 to 4, and A and n are defined as the same as described earlier).

[Tertiary Amine]

In the tertiary amine (V), (IV), (VII), at least one of $R^1$, $R^2$ and $R^3$ is R4; and with respect to $R^4$, the groups respectively represented by the above-mentioned formula (X) or (XI) are preferably used. The definition wherein is the same as described above.

Moreover, with respect to the alkyl group, the alkenyl group or the hydroxyalkyl group having carbon atoms of 1 to 6, represented by $R^1$, $R^2$ and $R^3$, an alkyl group or a hydroxyalkyl group having carbon atoms of 1 to 3 is preferably used, and a methyl group, ethyl group or hydroxyethyl group is more preferably used.

With respect to the above-mentioned tertiary amines, as the content of the tri-long-chain alkyl tertiary amines in which all the $R^1$, $R^2$ and $R^3$ are $R^4$ increases, the resulting quaternary ammonium salt has greater softness effects; therefore, the ratio of the tri-long-chain alkyl tertiary amines in the tertiary amines is preferably set to not less than 50 weight %, more preferably, not less than 85 weight %, most preferably, not less than 90 weight %. With respect to the tri-long-chain alkyl tertiary amines, those shown below are more preferably used.

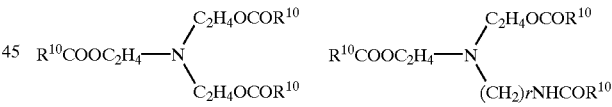

($R^{10}CO$ is defined as the same as described above, r represents 2 or 3.)

These tri-long-chain alkyl tertiary amines are obtained by, for example, a method in which tri-alkanol amine such as tri-ethanol amine is subjected to a tri-esterification process, or a method in which alkanol amines having an amino group within a molecule such as N-aminopropyl-N,N-hydroxyethylamine is subjected to a tri-acylation process. In this case, with respect to fatty acid or its ester to be used in the tri-esterification process or tri-acylation process, long-chain fatty acids having carbon atoms of 8 to 30, more preferably, 12 to 24, such as tallow fatty acid, hydrogenated tallow fatty acid, palm stearic acid, hydrogenated palm stearic acid or a mixture of two or more kinds selected from these, and its lower alkylester or fats and oils, may be used.

[Quaternizing reaction]

The aprotic solvent is preferably used at 5 to 90 weight %, more preferably, 9 to 70 weight %, with respect to the tertiary amine. With respect to the quaternizing agents used in the quaternizing reaction, dimethylsulfate, diethylsulfate, methylchloride, etc. are listed. The temperature at the time of the quaternizing reaction is preferably set to 30 to 150° C., more preferably, 50 to 120° C.

In the case when, with respect to the aprotic solvent, a solvent such as hexane that has low miscibility with water is used or when a solvent having odor such as acetone and tetrahydrofuran, is used, after the quaternizing process, the solvent is preferably evaporated away to form a lower alcohol solution such as isopropanol so as to be applied to the softener. In the case when the compound represented by the formula (XII) is used as the aprotic solvent, the solution, as it is, without distilling the solvent may be applied to the softener.

With respect to the quaternary ammonium salt obtained from the present invention, those having a ratio of not less than 50 weight %, more preferably, not less than 85 weight %, most preferably, not less than 90 weight %, of the tri-long-chain alkyl component in the quaternary ammonium salts, are preferably used.

EXAMPLES

In these examples, % represents weight reference unless otherwise defined.

Example 1

Triethanol amine (149 g) and 821 g of hydrogenated tallow fattyacid were used and subjected to an esterification reaction at 200° C. under nitrogen atmosphere for 10 hours to obtain N,N,N-tri (hydrogenated tallow alkanoyl oxyethyl) amine, and to this was further added 458 g of hexane, and this was subjected to a quaternizing reaction by using 126 g of dimethyl sulfate at 70° C. for 10 hours. After the reaction, the solvent was evaporated therefrom under reduced pressure, and to this was then added 184 g of isopropanol to obtain an isopropanol solution of quaternary ammonium salt. Table 1 shows the quaternizing ratio and its composition.

Here, the quaternizing ratio and compositions were measured by using an internal standard method based upon $^1$H-NMR method by using MERCURY 400 made by VARIAN.

Example 2

N,N-di(hydroxy ethyl)amino propyl amine (162 g) and 821 g of hydrogenated tallow fatty acid were used and subjected to an esterification reaction in the same manner as Example 1 to obtain N,N-di(hydrogenated tallow alkanoyl oxyethyl)-N-hydrogenated tallow ankanoyl aminopropyl amine, and to this was added 465 g of hexane, and this was subjected to a quaternizing reaction in the same manner as Example 1 by using 126 g of dimethyl sulfate, and after the solvent had been evaporated therefrom, to this was then added 186 g of isopropanol to obtain an isopropanol solution of quaternary ammonium salt. Table 1 shows the quaternizing ratio and its composition.

Example 3

N,N-di(hydroxy ethyl)-N-hydrogenated tallow alkanoyl amino ethylamine (404 g) and 547 g of hydrogenated tallow fatty acid were used and subjected to an esterification reaction in the same manner as Example 1 to obtain N,N-di(hydrogenated tallow alkanoyl oxyethyl)-N-hydrogenated tallow alkanoyl aminoethyl amine, and to this was added 458 g of hexane, and this was subjected to a quaternizing reaction in the same manner as Example 1 by using 126 g of dimethyl sulfate, and after the solvent had been evaporated therefrom, to this was then added 184 g of isopropanol to obtain an isopropanol solution of quaternary ammonium salt. Table 1 shows the quaternizing ratio and its composition.

Example 4

N,N-di (hydroxy ethyl)-N-hydrogenated tallow alkylamine (299 g) and 547 g of hydrogenated tallow fatty acid were used and subjected to an esterification reaction in the same manner as Example 1 to obtain N,N-di(hydrogenated tallow alkanoyl oxyethyl)-N-hydrogenated tallow alkylamine, and to this was added 405 g of hexane, and this was subjected to a quaternizing reaction in the same manner as Example 1 by using 126 g of dimethyl sulfate, and after the solvent had been evaporated therefrom, to this was then added 165 g of isopropanol to obtain an isopropanol solution of quaternary ammonium salt. Table 1 shows the quaternizing ratio and its composition.

Example 5

The same processes as Example 1 were carried out except that 458 g of acetone was used in place of hexane as a quaternizing solvent to obtain an isopropanol solution of quaternary ammonium salt. Table 1 shows the quaternizing ratio and its composition.

Example 6

The same processes as Example 1 were carried out except that 458 g of tetrahydrofuran was used in place of hexane as a quaternizing solvent to obtain an isopropanol solution of quaternary ammonium salt. Table 1 shows the quaternizing ratio and its composition.

Example 7

Triethanol amine (149 g) and 821 g of hydrogenated tallow fatty acid were used and subjected to an esterification reaction at 200° C. under nitrogen atmosphere for 10 hours to obtain N,N,N-tri (hydrogenated tallow alkanoyl oxyethyl) amine, and to this was further added 417 g of ethyleneoxide 12 mole adduct (HLB=14.0) of hydrogenated tallow fatty acid methyl ester as a quaternizing solvent, and this was subjected to a quaternizing reaction by using 126 g of dimethyl sulfate at 100° C. for 10 hours to obtain a solution of hydrogenated tallow fatty acid methyl ester ethyleneoxide 12 mole adduct of quaternary ammonium salt. Table 1 shows the quaternizing ratio and its composition.

Example 8

The same processes as Example 7 were carried out except that 417 g of ethylene glycol dimethylether was used in place of ethyleneoxide 12 mole adduct of hydrogenated tallow fatty acid methyl ester as a quaternizing solvent to obtain an ethyleneglycol dimethylether solution of quaternary ammonium salt. Table 1 shows the quaternizing ratio and its composition.

Example 9

The same processes as Example 8 were carried out except that 417 g of ethyleneglycol diacetate was used in place of ethylene glycol dimethylether as a quaternizing solvent to obtain an ethyleneglycol diacetate solution of quaternary ammonium salt. Table 1 shows the quaternizing ratio and its composition.

Example 10

N,N-di(hydroxyethyl)aminopropylamine (162 g) and 821 g of hydrogenated tallow fatty acid were used and the same process as Example 1 was carried out to obtain N,N-di(hydrogenated tallow alkanoyl oxyethyl)-N-hydrogenated tallow alkanoyl aminopropyl amine, and to this was further added 422 g of ethyleneoxide 12 mole adduct (HLB=14.0) of hydrogenated tallow fatty acid methyl ester as a quaternizing solvent, and this was subjected to a quaternizing reaction in the same manner as Example 7 to obtain a solution of hydrogenated tallow fatty acid methyl ester ethyleneoxide 12 mole adduct of quaternary ammonium salt. Table 1 shows the quaternizing ratio and its composition.

Example 11

N,N-di(hydroxy ethyl)-N-hydrogenated tallow alkanoyl amino ethylamine (404 g) and 547 g of hydrogenated tallow fatty acid were used and subjected to an esterification reaction in the same manner as Example 1 to obtain N,N-di(hydrogenated tallow alkanoyl oxyethyl)-N-hydrogenated tallow alkanoyl aminoethyl amine, and to this was further added 416 g of ethyleneoxide 12 mole adduct (HLB=14.0) of hydrogenated tallow fatty acid methyl ester as a quaternizing solvent, and this was subjected to a quaternizing reaction in the same manner as Example 7 to obtain a solution of hydrogenated tallow fatty acid methyl ester ethyleneoxide 12 mole adduct of quaternary ammonium salt. Table 1 shows the quaternizing ratio and its composition.

Example 12

The same processes as Example 7 were carried out except that as a quaternizing solvent, 417 g of ethyleneoxide 15 mole adduct (HLB=14.9) of hydrogenated tallow fatty acid methyl hydrogenated ester was used in place of ethyleneoxide 12 mole adduct of hydrogenated tallow fatty acid methyl hydrogenated ester to obtain a solution of hydrogenated tallow fatty acid methyl hydrogenated ester ethyleneoxide 15 mole adduct of quaternary ammonium salt. Table 1 shows the quaternizing ratio and its composition.

Example 13

The same processes as Example 7 were carried out except that as a quaternizing solvent, 417 g of ethyleneoxide 18 mole adduct (HLB=15.5) of hydrogenated tallow fatty acid methyl hydrogenated ester was used in place of ethyleneoxide 12 mole adduct of hydrogenated tallow fatty acid methyl ester to obtain a solution of hydrogenated tallow fatty acid methyl ester ethyleneoxide 18 mole adduct of quaternary ammonium salt. Table 1 shows the quaternizing ratio and its composition.

Example 14

The same processes as Example 7 were carried out except that as a quaternizing solvent, 417 g of ethyleneoxide 21 mole adduct (HLB=16.0) of hydrogenated tallow fatty acid methyl hydrogenated ester was used in place of ethyleneoxide 12 mole adduct of hydrogenated tallow fatty acid methyl hydrogenated ester to obtain a solution of hydrogenated tallow fatty acid methyl hydrogenated ester ethyleneoxide 21 mole adduct of quaternary ammonium salt. Table 1 shows the quaternizing ratio and its composition.

Example 15

The same processes as Example 7 were carried out except that as a quaternizing solvent, 417 g of ethyleneoxide 9 mole adduct (HLB=12.9) of hydrogenated tallow fatty acid methyl hydrogenated ester was used in place of ethyleneoxide 12 mole adduct of hydrogenated tallow fatty acid methyl hydrogenated ester to obtain a solution of hydrogenated tallow fatty acid methyl hydrogenated ester ethyleneoxide 9 mole adduct of quaternary ammonium salt. Table 1 shows the quaternizing ratio and its composition.

Example 16

The same processes as Example 1 were carried out except that 815 g of hydrogenated tallow fatty acid was used in place of hydrogenated tallow fatty acid in Example 1 to obtain a softener composition. Table 1 shows the quaternizing ratio and its composition.

Example 17

The same processes as Example 1 were carried out except that a mixture of 408 g of tallow fatty acid and 411 g of hydrogenated tallow fatty acid was used in place of hydrogenated tallow fatty acid in Example 1 to obtain a softener composition. Table 1 shows the quaternizing ratio and its composition.

Examples 18 to 23, 25, 26, 33, 34

The solution of quaternary ammonium salt obtained in each of Examples 1 to 6 and Examples, 8, 9, 16 and 17 was taken in a manner so as to set the total of quaternary ammonium salt to 5 g, and this was mixed with 2 g of stearyl alcohol ethyleneoxide 13 mole adduct (HLB=14.0), and after having been heated to 60° C., this was dripped into water at 60° C. in a molten state to prepare 100 g of a softener composition. The softness of these softener compositions was evaluated in the following methods. Table 2 shows the results of evaluation.

Examples 24, 27 to 32

The solution of quaternary ammonium salt obtained in each of Examples 7, 10 to 15 was taken in a manner so as to set the total of quaternary ammonium salt to 5 g, and after having been heated to 60° C., this was dripped into water at 60° C. in a molten state to prepare 100 g of a softener composition. The softness of these softener compositions was evaluated in the following methods. Table 2 shows the results of evaluation.

Comparative Example 1

Triethanol amine (149 g) and 547 g of hydrogenated tallow fatty acid were used and subjected to an esterification reaction at 200° C. under nitrogen atmosphere for 10 hours to obtain N,N-bis(hydrogenated tallow alkanoyl oxyethyl)-N-(2-hydroxyethyl) amine, and the same processes as Example 1 were carried out by using 184 g of isopropanol as a quaternizing solvent to obtain an isopropanol solution of quaternary ammonium salt. Table 1 shows the quaternizing ratio and its composition.

Comparative Example 2

The same processes as Example 1 were carried out except that 184 g of isopropanol was used in place of hexane as a quaternizing solvent to obtain an isopropanol solution of quaternary ammonium salt. Table 1 shows the quaternizing ratio and its composition.

Comparative Example 3

Triethanol amine (149 g) and 547 g of hydrogenated tallow fatty acid were used and subjected to an esterification reaction at 200° C. under nitrogen atmosphere for 10 hours, and to this was added 139 g of isopropanol, and this was subjected to a quaternizing reaction at 60° C. by using 126 g of dimethyl sulfate to obtain a propanol solution of N-methyl-N,N-bis(hydrogenated tallow alkanoyl oxyethyl)-N-(2-hydroxyethyl)ammonium methyl sulfate. It was found through NMR measurements that this solution had a long-chain alkyl quaternary ammonium salt content of 12%, a di-long-chain alkyl quaternary ammonium salt content of 35% and mono-long-chain alkyl quaternary ammonium salt content of 15%. The resulting isopropanol solution was taken in a manner so as to set the total amount of quaternary ammonium salt to 5 g, and this was mixed with 2 g of ethyleneoxide 12 mole adduct (HLB=14.0) of hydrogenated tallow fatty acid methyl ester, in the same manner as Example 1 to prepare 100 g of softener composition.

Comparative Example 4

Triethanol amine (149 g) and 547 g of hydrogenated tallow fatty acid were used and subjected to an esterification reaction at 200° C. under nitrogen atmosphere for 10 hours to obtain N,N-bis(hydrogenated tallow alkanoyl oxyethyl)-N-(2-hydroxyethyl) amine, and the same processes as Example 1 were carried out by using 330 g of hexane as a quaternizing solvent to obtain an isopropanol solution of quaternary ammonium salt. Table 1 shows the quaternizing ratio and its composition.

<Evaluation Method of Softness>

(1) Processing Method

Commercial cotton towels (1 kg) were put into a washing machine of 15 liters, and washed 5 times in hard water of 3.5 DH by using commercial detergent Attack (made by Kao Corp., registered trade name), and then to this was put 25 mL of the above-mentioned dispersing solution, and this was stirred for one minute at 25° C.

(2) Evaluation Method of Softness

The cloth, treated as described above, was dried and left still for 24 hours in a thermo-hygrostat of 25° C., 65% RH. Evaluation of softness was made on the cloth. The evaluation was made by comparing each pair of cloths using the cloth treated in Comparative Example 3 as a reference. The evaluation was carried out based upon the following criteria.

+2; softer than the reference

+1; slightly softer than the reference

0; as soft as the reference

−1; slightly harder than the reference

−2; harder than the reference

TABLE 1

|  | Quaternizing ratio (%) | Composition of quaternary ammonium salt solution (%) | | | |
| --- | --- | --- | --- | --- | --- |
|  |  | Tri-long-chain alkyl component | Di-long-chain alkyl component | Mono-long-chain alkyl component | Solvent |
| Example 1 | 95 | 67 | 11 | 0 | 15 |
| Example 2 | 93 | 66 | 11 | 0 | 15 |
| Example 3 | 91 | 64 | 11 | 0 | 15 |
| Example 4 | 90 | 64 | 10 | 0 | 15 |
| Example 5 | 89 | 63 | 10 | 0 | 15 |
| Example 6 | 93 | 66 | 10 | 0 | 15 |
| Example 7 | 97 | 63 | 9 | 0 | 27 |
| Example 8 | 95 | 67 | 10 | 0 | 15 |
| Example 9 | 91 | 65 | 10 | 0 | 15 |
| Example 10 | 95 | 57 | 10 | 0 | 28 |
| Example 11 | 93 | 56 | 9 | 0 | 29 |
| Example 12 | 95 | 58 | 10 | 0 | 27 |
| Example 13 | 93 | 57 | 9 | 0 | 27 |
| Example 14 | 91 | 55 | 9 | 0 | 27 |
| Example 15 | 91 | 54 | 9 | 0 | 27 |
| Example 16 | 94 | 66 | 11 | 0 | 15 |
| Example 17 | 94 | 66 | 11 | 0 | 15 |
| Comparative Example 1 | 80 | 12 | 35 | 15 | 15 |
| Comparative Example 2 | 65 | 46 | 7 | 0 | 15 |
| Comparative Example 3 | 80 | 12 | 35 | 15 | 15 |
| Comparative Example 4 | 85 | 18 | 36 | 15 | 15 |

Comparative Examples 5 to 8 (Evaluation of Compositions of Comparative Examples 1 to 4)

The solution of quaternary ammonium salt obtained in each of Comparative Examples 1 to 4 was taken in a manner so as to set the total of quaternary ammonium salt to 5 g, and this was mixed with 2 g of stearyl alcohol ethyleneoxide 13 mole adduct (HLB=14.0), and after having been heated to 60° C., this was dripped into water at 60° C. in a molten state to prepare 100 g of a softener composition. The softness of these softener compositions was evaluated in the following methods. Table 2 shows the results of evaluation.

TABLE 2

|  |  |  | Softness evaluation results | |
| --- | --- | --- | --- | --- |
|  | Cationic surfactant | Nonionic surfactant | Cotton towel | Acrylic jersey |
| Example 18 | Compound 1 | Compound 18 | +2 | +2 |
| Example 19 | Compound 2 | Compound 18 | +2 | +2 |

TABLE 2-continued

| | Cationic surfactant | Nonionic surfactant | Softness evaluation results | |
|---|---|---|---|---|
| | | | Cotton towel | Acrylic jersey |
| Example 20 | Compound 3 | Compound 18 | +2 | +2 |
| Example 21 | Compound 4 | Compound 18 | +2 | +1 |
| Example 22 | Compound 5 | Compound 18 | +2 | +1 |
| Example 23 | Compound 6 | Compound 18 | +2 | +1 |
| Example 24 | Compound 7 | Compound 19 | +2 | +1 |
| Example 25 | Compound 8 | Compound 18 | +2 | +1 |
| Example 26 | Compound 9 | Compound 18 | +1 | +1 |
| Example 27 | Compound 10 | Compound 19 | +2 | +2 |
| Example 28 | Compound 11 | Compound 19 | +2 | +2 |
| Example 29 | Compound 12 | Compound 20 | +1 | 0 |
| Example 30 | Compound 13 | Compound 21 | +1 | +1 |
| Example 31 | Compound 14 | Compound 22 | +1 | +1 |
| Example 32 | Compound 15 | Compound 23 | +1 | +1 |
| Example 33 | Compound 16 | Compound 18 | +1 | +1 |
| Example 34 | Compound 17 | Compound 18 | +2 | +1 |
| Comparative Example 5 | Compound of Comparative Example 5 | Compound 18 | 0 | 0 |
| Comparative Example 6 | Compound of Comparative Example 6 | Compound 18 | −2 | −2 |
| Comparative Example 7 | Compound of Comparative Example 7 | Compound 19 | 0 | 0 |
| Comparative Example 8 | Compound of Comparative Example 8 | Compound 18 | 1 | 0 |

Compound 18: 13 mole adduct of stearyl alcohol ethylene oxide
Compound 19: 12 mole ethylene oxide adduct of hydrogenated tallow fatty acid methyl ester
Compound 20: 15 mole ethylene oxide adduct of hydrogenated tallow fatty acid methyl ester
Compound 21: 18 mole ethylene oxide adduct of hydrogenated tallow fatty acid methyl ester
Compound 22: 21 mole ethylene oxide adduct of hydrogenated tallow fatty acid methyl ester
Compound 23: 9 mole ethylene oxide adduct of hydrogenated tallow fatty acid methyl ester

We claim:

1. A softener composition comprising the following components (A') and (B'):

(A'): a cationic surfactant comprising at least one selected from the group consisting of quaternary ammonium salts represented by the formulae (I), (II) or (III)

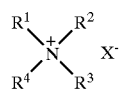

(I)

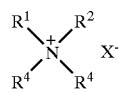

(II)

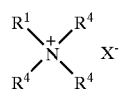

(III)

and at least one selected from the group consisting of amines or salts thereof represented by the following formulae (V), (VI) or (VII), where the ratio of the total mole number of the quaternary ammonium salts to the total molar number of amines or the salts thereof is 99.9:0.1 to 70:30 and the ratio of the quaternary ammonium salts represented by the formula (I) to the total amount of the quaternary ammonium salts represented by the formulae (I), (II) and (III) exceeds 50 weight % and the ratio of (III) to the sum total of (I), (II) and (III) is not more than 10%:

(V)

(VI)

(VII)

wherein $R^1$, $R^2$ and $R^3$ represent a long-chain alkyl or alkenyl group having the total carbon atoms of 8 to 40, which are the same as or different from one another and may be intersected by an ether group, an ester group or an amide group; $R^4$ represents an alkyl group, an alkenyl group or a hydroxy alkyl group, having 1 to 6 carbon atoms, plural $R^4$'s being the same as or different from one another; and $X^-$ represents an anionic group; and (B'): at least one nonionic surfactant selected from the group consisting of compounds represented by formulae (VIII) and (IX):

(VIII)

(IX)

wherein, $R^7$ represents an alkyl group or an alkenyl group having carbon atoms of 8 to 22, A represents an alkylene group having 2 to 4 carbon atoms, n represents a number of 4 to 100 on the average value, p and q are a number of 1 to 50 on the average value, being the same as or different from each other, and plural A's may be the same as or different from one another.

2. The softener composition according to claim 1, wherein the ratio of the total mole number of the quaternary ammonium salts represented by the formulae (I), (II) and (III) to the total mole number of the amine salts represented by the formulae (V), (VI) and (VII) is 99:1 to 80:20.

3. The softener composition of claim 1, or claim 2, wherein $R^1$, $R^2$ and $R^3$ are the same as or different from one another and are groups represented by the following formula (X) or (XI):

(X)

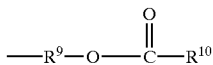

(XI)

wherein $R^8$ and $R^9$ are the same as or different from each other and represent an alkylene group having 2 to 6 carbon atoms and $R^{10}CO$ represents a residual group resulting from a fatty acid having 8 to 30 carbon atoms from which a hydroxyl group has been excluded.

4. The softener composition according to claim 1 or claim 2, wherein said surfactant that is a compound represented by the formula (VIII) or (IX) has an HLB of 9 to 17.

5. The softener composition according to claim 1, or claim 2, wherein the blending ratio of the component (A') to the component (B') which is (A')/(B') by weight is 50/1 to 1/2.

6. The softener composition according to claim 1 or claim 2, wherein the blending ratio of the component (A') to the composition is 3 to 50 weight %.

7. A softener composition comprising the following components (A') and (B'):

(A') a cationic surfactant comprising at least one selected from the group consisting of quaternary ammonium salts represented by the formulae (I), (II) or (III)

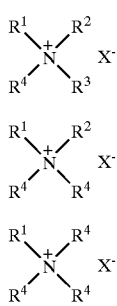

(I)

(II)

(III)

and at least one selected from the group consisting of amines or salts thereof represented by the following formulae (V), (VI) or (VII), where the ratio of the total mole number of the quaternary ammonium salts to the total molar number of amines or the salts thereof is 99.9:0.1 to 70:30 and the ratio of the quaternary ammonium salts represented by the formula (I) to the total amount of the quaternary ammonium salts represented by the formulae (I), (II) and (III) exceeds 50 weight % and the ratio of (III) to the sum total of (I), (II) and (III) is not more than 10%:

(V)

(VI)

(VII)

wherein $R^1$, $R^2$ and $R^3$ represent a long-chain alkyl or alkenyl group having the total carbon atoms of 8 to 40, which are the same as or different from one another and may be intersected by an ether group, an ester group or an amide group; $R^4$ represents an alkyl group, an alkenyl group or a hydroxy alkyl group, having 1 to 6 carbon atoms, plural $R^4$'s being the same as or different from one another; and $X^-$ represents an anionic group; and (B'): at least one nonionic surfactant selected from the group consisting of compounds represented by formulae (VIII) and (IX):

$R^7O\,(AO)nH$ (VIII)

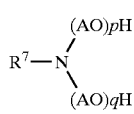

(IX)

wherein, $R^7$ represents an alkyl group or an alkenyl group having carbon atoms of 8 to 22, A represents an alkylene group having 2 to 4 carbon atoms, n represents a number of 4 to 100 on the average value, p and q are a number of 1 to 50 on the average value, being the same as or different from each other, and plural A's may be the same as or different from one another; and wherein, the blending ratio in the softener composition of the component (A') to the component (B') by weight, which is (A')/(B'), is 50/1 to 1/2, and the blending ratio of the component (A') to the softener composition is 3 to 50 weight %.

8. The softener composition according to claim 1 or 7, wherein prior to a mixing with water, a total amount of the component (A') and the component (B') in the softener composition is not less than 70 weight %.

* * * * *